United States Patent
Rathjen

(10) Patent No.: US 11,331,218 B2
(45) Date of Patent: *May 17, 2022

(54) OPHTHALMOLOGICAL DEVICE FOR TREATING EYE TISSUE

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/002,182

(22) Filed: Aug. 25, 2020

(65) Prior Publication Data

US 2020/0383829 A1 Dec. 10, 2020

Related U.S. Application Data

(63) Continuation of application No. 16/278,816, filed on Feb. 19, 2019, now Pat. No. 10,786,388, which is a
(Continued)

(51) Int. Cl.
*A61F 9/008* (2006.01)

(52) U.S. Cl.
CPC .... *A61F 9/008* (2013.01); *A61F 2009/00897* (2013.01)

(58) Field of Classification Search
CPC .................. A61F 9/008; A61F 2009/00897
See application file for complete search history.

(56) References Cited

U.S. PATENT DOCUMENTS

| 2003/0074150 A1 | 4/2003 | Goldstein et al. |
| 2004/0070761 A1 | 4/2004 | Horvath et al. |

(Continued)

FOREIGN PATENT DOCUMENTS

| DE | 10349296 A1 | 5/2005 |
| EP | 1034755 A1 | 9/2000 |

(Continued)

OTHER PUBLICATIONS

Pi-USA, Active Optic/Fast Tip-Tilt Piezo Steering Mirrors, https://web.archive.org/web/20111119124958/http://www.pi-usa.us/products/Active_Optics_Steering_Mirrors/index.php, Nov. 19, 2011.

*Primary Examiner* — Nathan J Jenness
(74) *Attorney, Agent, or Firm* — Banner & Witcoff, Ltd.

(57) ABSTRACT

An ophthalmological device for treating eye tissue with laser pulses comprises a projection optical unit for focused projection of the laser pulses, a scanner system for dynamically deflecting the laser pulses and a zoom system, which is arranged between the projection optical unit and the scanner system and which is configured to adjust the focused projection of the laser pulses in the projection direction in different zoom settings. The ophthalmological device moreover comprises a displacement device, which is configured to displace the scanner system depending on the zoom setting of the zoom system. What the displacement of the scanner system coupled to the zoom setting of the zoom system renders possible is the adaptation of the position of the scanner system in a dynamic and synchronized fashion to the setting of the zoom system and hence to the current position of the virtual entry pupil of the zoom system.

19 Claims, 2 Drawing Sheets

Related U.S. Application Data continuation of application No. 14/154,614, filed on Jan. 14, 2014, now Pat. No. 10,245,180.

(60) Provisional application No. 61/753,141, filed on Jan. 16, 2013.

(56) References Cited

U.S. PATENT DOCUMENTS

| | | | |
|---|---|---|---|
| 2005/0288745 A1* | 12/2005 | Andersen | A61F 9/00821 607/86 |
| 2007/0129709 A1 | 6/2007 | Andersen et al. | |
| 2008/0165320 A1 | 7/2008 | Heiberger | |
| 2011/0118713 A1* | 5/2011 | Raksi | A61F 9/00814 606/6 |
| 2011/0245817 A1* | 10/2011 | Yokosuka | A61F 9/00821 606/4 |
| 2012/0271286 A1* | 10/2012 | Curatu | G02B 27/0031 606/5 |

FOREIGN PATENT DOCUMENTS

| | | |
|---|---|---|
| EP | 1584310 A1 | 10/2005 |
| WO | 2011017000 A2 | 2/2011 |
| WO | 2011/091326 A1 | 7/2011 |
| WO | 2012/178054 A1 | 12/2012 |

* cited by examiner

OPHTHALMOLOGICAL DEVICE FOR TREATING EYE TISSUE

CROSS REFERENCE TO RELATED APPLICATIONS

The present application is a continuation application of prior U.S. application Ser. No. 16/278,816, filed Feb. 19, 2019, which is a continuation application of U.S. application Ser. No. 14/154,614, filed Jan. 14, 2014, now U.S. Pat. No. 10,245,180 B2, issued Apr. 2, 2019, which claims benefit of U.S. Provisional Application No. 61/753,141, filed Jan. 16, 2013, the disclosures of which are herein incorporated herein by reference in their entireties.

TECHNICAL FIELD

The present disclosure relates to an ophthalmological device for treating eye tissue with laser pulses. The present disclosure more particularly relates to an ophthalmological device for treating eye tissue with laser pulses, comprising a scanner system for dynamically deflecting the laser pulses and a projection optical unit for focused projection of the laser pulses.

BACKGROUND

When treating eye tissue with pulsed laser beams, use is made of focusing devices in order to adjust the focusing range. Particularly in the case of ophthalmological laser systems with extended fields of application, which, in addition to the treatment of eye tissue of the cornea, should enable focus positions extending beyond the cornea, e.g. for lens surgery or for the treatment of other eye regions situated behind the cornea, provision is made for focusing devices in the beam path between the laser source and the projection optical unit in order to extend or adjust the focusing range. These focusing devices carry out zoom movements or zoom functions for adjusting the focus depth in the optical path so that the focused projection is displaced in the projection direction. The zoom movements or zoom functions comprise a displacement of one or more optical elements along the optical axis of a system. Considered in general, a zoom action can be carried out by displaceable lenses or mirrors, but also by other optical elements, for example by deformable lenses, deformable mirrors, SLM (spatial light modulator) systems or systems with dynamic modulation of the refractive index. Hence general optical systems which adjust the focal length thereof are considered to be zoom systems. Depending on the technical implementation, a different number of elements are required for this. Hence the focus position is determined by the zoom setting of the zoom system, with the zoom setting being determined, depending on the technical implementation, by zoom movements of lenses and/or mirrors or zoom actions or zoom functions for setting deformable lenses, deformable mirrors, SLM systems or refractive index modulators.

WO2011/017000 describes an optical system with a scanner system for ophthalmological laser surgery, which comprises a zoom system which enables a depth scan or z-scan beyond the region of the cornea down into the depths of the lens, with the focus position being adjusted over an extended range from the cornea into the lens. In the optical system as per WO2011/017000, the position of the virtual entry pupil of the zoom system is modified by the zoom actions carried out during the depth scan or z-scan. Here, depending on the current setting of the zoom system, this causes increased distances of the scanner system from the virtual entry pupil of the zoom system. The upshot of this is that the zoom system must have a design with the larger diameter and hence it is more expensive (the costs increase at least with the square of the diameter). Furthermore, use has to be made of larger scanner systems, e.g. larger mirrors, or other measures have to be taken so that the laser beams deflected by the scanner system can enter the entry pupil of the zoom system without restrictions. In accordance with WO2011/017000, two additional scanning axes are proposed to this end, which re-deflect the scanned beam onto the optical axis in such a way that, in every zoom position, the deflected laser beam intersects the optical axes at the point where the current entry pupil of the zoom system is situated. With the interaction of the four scanner axes, it is possible, firstly, to set the deflection angle (scanning angle) in two spatial directions and, secondly, also to determine the point of intersection of the deflected laser beam with the optical axis. However, in this case, the advantage of a more compact optical system is bought by the disadvantage of a significantly increased control complexity and additional scanner systems.

DESCRIPTION OF THE DISCLOSURE

The present disclosure describes an ophthalmological device for treating eye tissue with laser pulses, which does not have at least some of the disadvantages of the known systems. In particular, the present disclosure describes an ophthalmological device for treating eye tissue with laser pulses, which enables an adjustment of the focus position of the laser pulses in the projection direction, without having to provide enlarged and/or additional scanner mirrors to this end or minimize the diameter and the size of the zoom system.

In accordance with the present disclosure, these goals are achieved by the features of the independent claims. Further advantageous embodiments moreover emerge from the dependent claims and the description.

An ophthalmological device for treating eye tissue with laser pulses comprises a scanner system for dynamically deflecting the laser pulses, a projection optical unit for focused projection of the laser pulses and a zoom system, which is arranged between the scanner system and the projection optical unit and which is configured to adjust the focused projection of the laser pulses in the projection direction in different zoom settings.

The aforementioned goals are, in particular, achieved by the present disclosure by virtue of the fact that the ophthalmological device moreover comprises a displacement device, which is configured to displace the scanner system depending on the zoom setting of the zoom system.

A simple displacement movement of the scanner system, which is only dependent on the zoom setting, i.e., for example, on the zoom movement, enables a significantly simpler connection of the scanner system to the zoom system than the solution of a synchronized movement of four mirror axes described in the prior art. Compared to the prior art, it is possible to save corresponding scanner systems for two mirror axes, which reduces the thermal load on the optical systems due to the scanner drives, and there is no need to provide a control with closed-loop control algorithms for a complex, four-axes scanner system. Moreover, it is also possible to reduce the instrument costs overall and higher dynamics (speed) can be achieved by the enabled use of small mirrors.

In a preferred embodiment variant, the displacement device is configured to displace the scanner system along an optical axis of the zoom system. The displacement device preferably comprises a drive for displacing the scanner system.

In a further embodiment variant, the displacement device is configured to displace the scanner system in a synchronized manner with the zoom setting of the zoom system.

In a further embodiment variant, the displacement device is configured to displace the scanner system in a synchronized manner with the zoom setting of the zoom system.

In one embodiment variant, the displacement device is configured to displace the scanner system in a synchronized manner with the adjustment of the focused projection brought about by the zoom system.

In a further embodiment variant, the displacement device is configured to displace the scanner system depending on the position of a virtual entry pupil of the zoom system. In one embodiment variant, the displacement device is configured to displace the scanner system along an optical axis of the zoom system to a defined position in respect of the virtual entry pupil of the zoom system. Hence, the whole scanner system can be displaced along the optical axis using a simple translation in order to position the deflection mirrors as closely as possible to or in the virtual entry pupil of the zoom system.

In a further embodiment variant, the ophthalmological device comprises a control module, which is configured to generate positioning signals for controlling a drive provided for displacing the scanner system, depending on control signals for the zoom system or on feedback signals from the zoom system.

In one embodiment variant, the scanner system comprises a mirror which is rigid in relation to the scanner system, also moved in the case of a displacement of the scanner system and configured to guide the laser pulses from a laser source to a movable deflection mirror of the scanner system.

In a further embodiment variant, the ophthalmological device comprises an optical transmission system, which is interposed between the scanner system and the zoom system and configured to transmit the laser pulses deflected by the scanner system to the zoom system. By way of example, the optical transmission system is arranged in a mechanical support system, by means of which the scanner system and the zoom system are mechanically connected to one another.

In one embodiment variant, the ophthalmological device comprises an optical transmission system, which is interposed between the zoom system and the projection optical unit and configured to transmit the laser pulses from the zoom system to the projection optical unit. By way of example, the optical transmission system is arranged in a mechanical support system, by means of which the projection optical unit and the zoom system are mechanically connected to one another.

In a further embodiment variant, the ophthalmological device comprises a compensation system, which is configured to optically compensate aberrations of the zoom system depending on displacement and deflection angle of the scanner system.

By way of example, the ophthalmological device comprises a laser source, which is configured to generate femtosecond laser pulses. The scanner system comprises at least one movable mirror for dynamically deflecting the laser pulses. The projection optical unit is configured to project the laser pulses into the eye tissue in a focused manner in order to break down eye tissue.

BRIEF DESCRIPTION OF THE DRAWINGS

In the following text, an embodiment of the present disclosure is described on the basis of an example. The exemplary embodiment is illustrated by the following attached figures.

WAYS OF IMPLEMENTING THE DISCLOSURE

Figure 1:
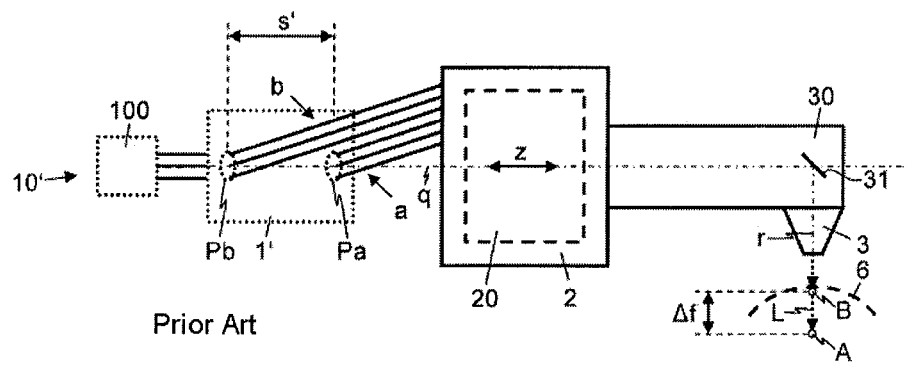
FIG. 1 schematically shows a cross section of an ophthalmological device in accordance with the prior art for treating eye tissue with laser pulses, having a scanner system and a zoom system.
Figure 2:
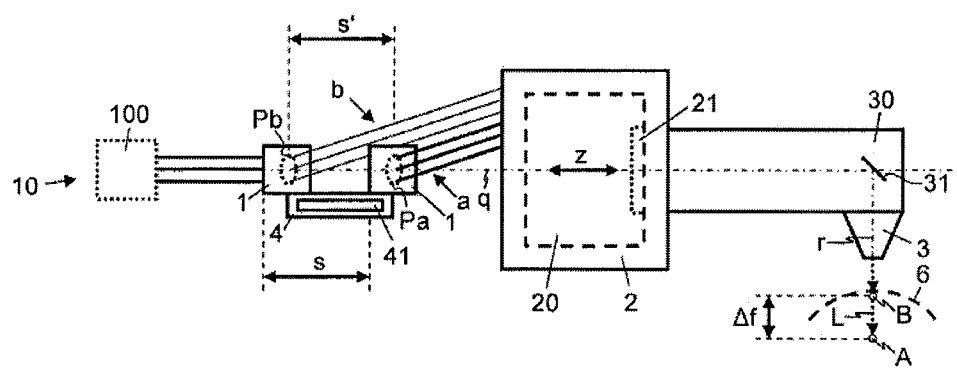
FIG. 2 schematically shows a cross section of an ophthalmological device for treating eye tissue with laser pulses, having a displacement device for displacing the scanner system depending on settings of the zoom system.
Figure 3:
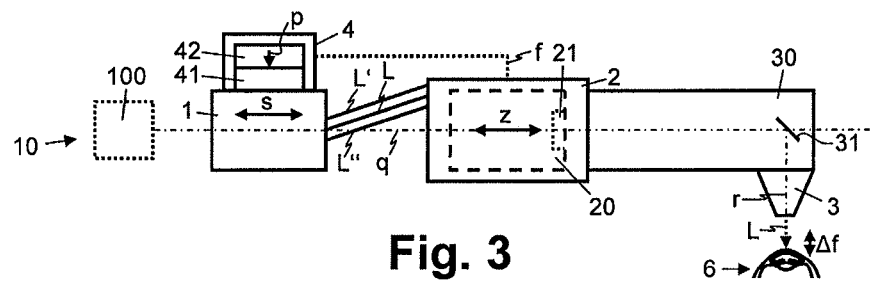
FIGS. 3-7 schematically show a cross section of different embodiments of an ophthalmological device for treating eye tissue with laser pulses, having a displacement device for displacing the scanner system depending on settings of the zoom system.
Figure 4:
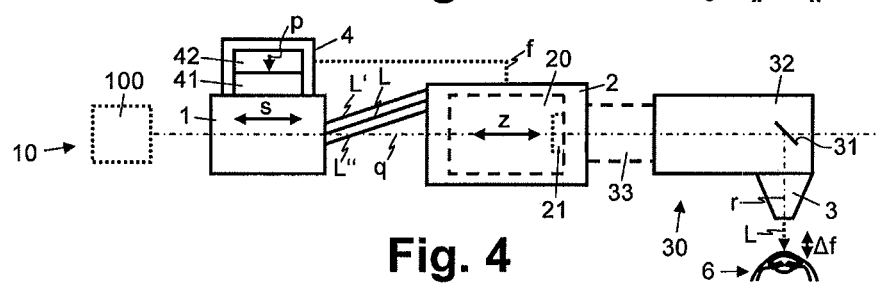

In FIG. 1, reference sign 10' relates to an ophthalmological device in accordance with the prior art for treating eye tissue 6 with laser pulses L. The ophthalmological device 10' comprises a laser source 100, a projection optical unit 3 for focused projection of the laser pulses L, a scanner system 1' for dynamically deflecting the laser pulses L and a focusing device 2 with an optical zoom system 20, which is arranged in the beam path between the projection optical unit 3 and the scanner system 1' and which is configured to adjust the focused projection of the laser pulses L in projection direction r, depending on the schematically depicted zoom setting z of the zoom system 20, in order to set different focus depths A, B, as indicated by the focus adjustment Δf.

By way of example, the zoom system 20 comprises several (typically two, but also three or four if, in addition to the focus position, other optical parameters such as beam divergence or focus diameter are also to be set and/or if aberrations are to be compensated for) lenses and/or lens groups, which are displaceable along the optical axis q and which are configured to modify and determine the zoom setting z of the zoom system 20 by zoom movements, in order thereby to adjust the focused projection of the laser pulses L in projection direction r and generate a focus adjustment Δf for different focus depths A, B. As mentioned at the outset, the zoom system 20 can also comprise other optical elements in addition to or instead of displaceable lenses in alternative embodiments variants, for example mirrors, deformable lenses, deformable mirrors, SLM (spatial light modulator) systems or systems with dynamic modulation of the refractive index, in order to modify and determine the zoom setting z of the zoom system 20 by means of corresponding zoom actions or zoom functions.

As depicted in FIGS. 1 to 7, the zoom system 20 is arranged between the projection optical unit 3 and the scanner system 1, 1'. However, a person skilled in the art will understand that, depending on the embodiment variant, the zoom system 20 can also have parts, e.g. lenses and/or lens groups, arranged upstream of the scanner system 1, 1', i.e. arranged closer to the laser source 100 on the optical path.

The zoom system 20 has a changeable entry pupil Pa, Pb. The entry pupil Pa, Pb of an optical system is an imagined, i.e. virtual, stop, which restricts the beams of the optical system. As can be seen from FIG. 1, the adjustment of the focused projection of the laser pulses L by the zoom system 20 brings about not only the focus adjustment Δf but also a displacement s' of the position of the (virtual) entry pupil Pa, Pb of the zoom system 20 along the optical axis q of the zoom system 20. This increases the distance between the scanner system 1' and the zoom system 20, which (in the depicted example) makes an enlargement of the diameter of the zoom system 20 necessary and possibly also requires a larger scanner aperture of the scanner system 1' (otherwise the scanning angle would have to be reduced). What holds true in general is that the diameter of the zoom system 20 has to be enlarged if the scanner aperture does not coincide with the entry pupil of the zoom system 20 (i.e. does not lie at the same location in the case where the diameter is the same). Otherwise the scanned beam is cut off on physical stops in the zoom system 20, which is also known by the term vignetting. The beam profiles in FIG. 1 only schematically depict the usable beam cross sections. A disadvantage when using a scanning mirror (with beam coupling from the side) is also that only part of the radiated laser power is transmitted. The effect that the size of the entry pupil Pa, Pb can also change depending on the zoom system 20 was not depicted in FIG. 1. The relationships explained here show that an optimal design of scanner and zoom with the goal of minimizing both the scanner apertures and the diameter of the zoom system 20 cannot be realized by the use of two scanning axes as known in the prior art. Both an enlargement of the zoom system 20 and an enlargement of deflection mirrors are connected with increased costs and the disadvantages already described at the outset.

In FIGS. 2 to 7, reference sign 10 relates to an ophthalmological device for treating eye tissue 6 with laser pulses L, which device, in contrast to the prior art, has a displacement device 4 in addition to laser source 100, projection optical unit 3, scanner system 1 and focusing device 2 with optical zoom system 20, which displacement device is configured to displace the scanner system 1 along the optical axis q of the zoom system 20, as indicated by the displacement (translational movement) denoted by s.

The scanner system 1 comprises one or more deflection apparatuses, e.g. movable deflection mirrors, which are configured to deflect the laser pulses L dynamically in at least one deflection direction and thereby guide the laser beam formed by the laser pulses L along at least one scanning direction by modifying the deflection angle (scanning angle in relation to the optical axis). Depending on the embodiment variant, the scanner system 1 comprises one or more galvanoscanners, polygon scanners, resonance scanners, AOM (acoustic-optic modulator) scanners, EOM (electro-optic modulator) scanners and/or SLM (spatial light modulator) scanners.

The laser source 100 is configured to generate a laser beam pulsed by laser pulses L, e.g. by femtosecond laser pulses.

The displacement device 4 is configured, in particular, to displace the scanner system 1 dependent (i) on the current zoom setting z of the zoom system 20. That is to say, the displacement device 4 is configured to displace the scanner system 1 coupled to (i) the zoom movement/zoom function carried out by the zoom system 20 or (ii) the displacement s of the virtual entry pupil Pa, Pb of the zoom system 20 brought about by the zoom movement/zoom function or (iii) the focus adjustment Δf brought about by the zoom movement/zoom function.

As depicted schematically in FIGS. 2 to 7, the displacement device 4 comprises a drive 41, coupled to the scanner system 1, for displacing the scanner system 1. As depicted schematically in FIGS. 3 to 7, the displacement device 4 moreover comprises a control module 42, which is configured to control the drive 41 depending on the current zoom setting z of the zoom system 20, i.e. depending on the zoom movement/zoom function of the zoom system 20. The control module 42 comprises one or more circuits, for example a processor with stored computer program code, a programmed logic circuit and/or an electronic circuit, which is configured to control the drive 41 for displacing the scanner system 1 depending on the current zoom setting z of the zoom system 20, i.e. depending on the zoom movement/zoom function of the zoom system 20. To this end, the control module 42 generates positioning signals p, which are fed to the drive 41 of the displacement device 4 for carrying out the displacement s. In one embodiment variant, the control module 42 is configured to generate the positioning signals p for the drive 41 depending on focusing signals f, which are fed to the zoom system 20, for determining the current zoom setting z, by means of which a focus adjustment Δf for setting the desired projection focus in projection direction r is obtained. Here, the focusing signals f are generated in the control module 42 itself or in another control unit, for example in the focusing device 2, which is independent of the control module 42. In an alternative embodiment, the zoom system 20 generates a feedback signal, which continuously provides the control module 42 with the current zoom setting z. Accordingly, the control module 42 controls the drive 41 depending on the feedback signal, which specifies the current zoom setting z. By displacing s the scanner system 1 depending on the current zoom setting z of the zoom system 20, it is possible to adapt the position of the scanner system 1 in a dynamic and synchronized fashion to the current position of the virtual entry pupil Pa, Pb of the zoom system 20. Here, the scanner system 1 or the deflection mirrors thereof are continuously positioned as close as possible to the virtual entry pupil Pa, Pb of the zoom system 20, for example at a position with a fixedly defined distance value from the virtual entry pupil Pa, Pb or directly into the virtual entry pupil Pa, Pb. Furthermore, the scanner displacement can also occur in discrete steps. In the case of anterior chamber surgery of cornea and lens at least two scanner positions would have to be met for this purpose, one for the cornea and one for the lens.

The zoom system 20 optionally comprises a compensation system 21, which is configured to optically compensate aberrations of the zoom system 20 depending on the displacement s (and therefore implicitly also depending on the current zoom setting z of the zoom system 20) and/or deflection angle(s) of the scanner system 1. The compensation system 21 comprises one or more circuits, for example a processor with stored computer program code, a programmed logic circuit and/or an electronic circuit, which are configured to control the zoom system 20 depending on the current displacement s and the current deflection angle or angles of the scanner system 1 in such a way that aberrations of the zoom system 20 are compensated for, which would be caused by the relevant displacement s and the relevant deflection angle or angles of the scanner system 1. To this end, in one embodiment variant, the compensation system 21 comprises a compensation table or compensation function, which in each case specifies correction values or compensated focusing signals f for controlling the zoom system 20 for various displacements s and deflection angles of the scanner system 1. In another embodiment variant, the displacement of the scanner system s itself is used to compensate for aberrations.

As depicted schematically in FIGS. 1 to 7, the ophthalmological device 10, 10' comprises an optical transmission system 30, by means of which the laser pulses L are guided from the focusing device 2 or from the zoom system 20 to the projection optical unit 3.

As depicted schematically in FIGS. 4 to 7, the optical transmission system 30 comprises, depending on the embodiment variant, an optional support system 33 and an application head 32, wherein the optical elements of the optical transmission system 30 are arranged in the support system 33 and/or in the application head 32 and the projection optical unit 3 is attached to the application head 32 or integrated into the application head 32. Depending on the embodiment variant, the optical elements of the optical transmission system 30 comprise one or more mirrors for deflecting the laser beam or the laser pulses L and one or more lenses, for example for generating one or more intermediate focuses in the beam path between the focusing device 2 or the zoom system 20 and the projection optical unit 3. In a particularly simple embodiment, the optical transmission system 30 comprises a deflection mirror 31 as sole optical element. In various embodiment variants, the support system 33 comprises a rigid support arm, a multi-member, movable hinged arm or only a coupling system for fixed or detachable attachment of the application head 32 on the focusing device 2.

Figure 5:
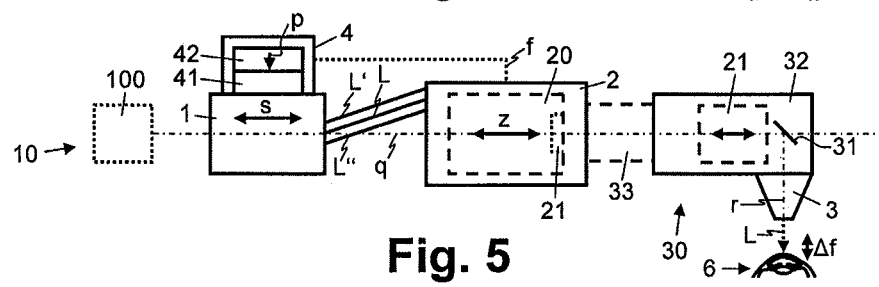

As depicted schematically in FIG. 5, the optical transmission system 30 comprises a further zoom system 21 in one embodiment variant, which further zoom system is configured to adjust the focused projection of the laser pulses L in projection direction r in order to set different focus depths.

Figure 6:
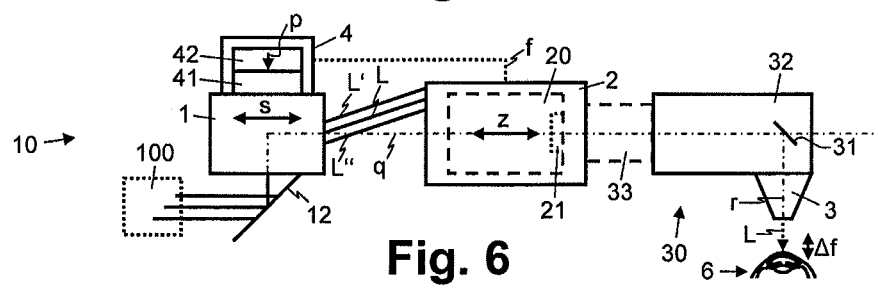
Figure 7:
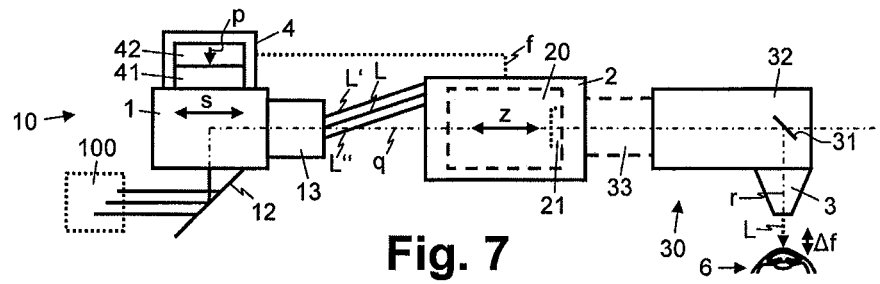

As depicted schematically in FIGS. 6 and 7, the ophthalmological device 10 comprises a deflection mirror 12 in one embodiment variant, which deflection mirror is fixedly attached to the scanner system 1 and configured to be immobile in respect of the scanner system 1. By means of this deflection mirror 12 of the scanner system 1, the laser pulses L or the laser beam are fed from the laser source 100 to the scanner system 1, in particular to a movable mirror of the scanner system 1.

As depicted schematically in FIG. 7, the ophthalmological device 10 comprises a further optical transmission system 13 in one embodiment variant, which optical transmission system is interposed in the beam path between the scanner system 1 and the focusing device 2 or the zoom system 20. Depending on the embodiment variant, the optical elements of this further optical transmission system 13 comprise one or more mirrors for deflecting the laser beam or the laser pulses L and/or one or more lenses, for example for generating one or more intermediate focuses in the beam path between the scanner system 1 and the focusing device 2 or the zoom system 20. By way of example, the further optical transmission system 13 is arranged in a mechanical support system, which mechanically connects the scanner system 1 and the zoom system 20 to one another.

What is claimed is:

1. An ophthalmological device for treating eye tissue with laser pulses, the ophthalmological device comprising:
    a laser source configured to generate the laser pulses;
    a scanner system comprising at least one movable deflection mirror configured to dynamically deflect the laser pulses;
    a projection optical unit for focused projection of the laser pulses in a projection direction;
    a zoom system, which is arranged downstream of the scanner system and upstream of the projection optical unit, and configured to adjust the focused projection of the laser pulses in the projection direction in different zoom settings, wherein the zoom system has an optical axis and a virtual entry pupil which moves along the optical axis with the different zoom settings; and
    a displacement device configured to displace the scanner system, with respect to the virtual entry pupil of the zoom system, along the optical axis of the zoom system depending on the zoom setting of the zoom system.

2. The ophthalmological device of claim 1, wherein the displacement device is configured to displace the scanner system with respect to the virtual entry pupil of the zoom system, with a translatory motion of the scanner system along the optical axis of the zoom system, depending on the zoom setting of the zoom system.

3. The ophthalmological device of claim 1, wherein the displacement device is configured to displace the scanner system in a synchronized manner with the zoom setting of the zoom system.

4. The ophthalmological device of claim 1, wherein the displacement device is configured to displace the scanner system in a synchronized manner with an adjustment of the focused projection brought about by the zoom system.

5. The ophthalmological device of claim 1, wherein the displacement device comprises a drive coupled to the scanner system and configured to displace the scanner system along the optical axis of the zoom system; and
    the displacement device further comprises one or more circuits configured to generate positioning signals for controlling the drive depending on control signals for the zoom system or on feedback signals from the zoom system.

6. The ophthalmological device of claim 1, wherein the displacement device comprises:
    a drive coupled to the scanner system and configured to displace the scanner system along the optical axis of the zoom system; and
    one or more circuits configured to control the drive to displace the scanner system along the optical axis to defined scanner positions with respective distances from the virtual entry pupil, the defined scanner positions including at least one of: a scanner position for performing cornea surgery or a scanner position for performing lens surgery.

7. The ophthalmological device of claim 1, further comprising an optical transmission system, which is interposed between the scanner system and the zoom system and configured to transmit the laser pulses deflected by the scanner system to the zoom system.

8. The ophthalmological device of claim 1, further comprising an optical transmission system, which is interposed between the zoom system and the projection optical unit and configured to transmit the laser pulses from the zoom system to the projection optical unit.

9. The ophthalmological device of claim 8, wherein the optical transmission system is arranged in a mechanical support system, by means of which the projection optical unit and the zoom system are mechanically connected to one another.

10. The ophthalmological device of claim 1, further comprising a compensation system configured to optically compensate aberrations of the zoom system depending on a displacement of the scanner system and a deflection angle of the scanner system.

11. The ophthalmological device of claim 10, wherein the compensation system comprises a circuit configured to control the zoom system depending on the displacement and the deflection angle of the scanner system, such as to compensate for the aberrations of the zoom system, caused by the displacement of the scanner system and the deflection angle of the scanner system, using a compensation table or compensation function which define correction values for controlling the zoom system for various displacements of the scanner system and deflection angles of the scanner system.

12. The ophthalmological device of claim 1, wherein the displacement device comprises:
a drive coupled to the scanner system and configured to displace the scanner system along the optical axis of the zoom system, and
one or more circuits configured to control the drive to displace the scanner system along the optical axis of the zoom system using a current zoom setting of the zoom system to adapt a position of the scanner system, with respect to a current position of the virtual entry pupil of the zoom system, for continuously maintaining a value of distance of the scanner system from the virtual entry pupil of the zoom system.

13. The ophthalmological device of claim 1, wherein the laser source is configured to generate femtosecond laser pulses, and the projection optical unit is configured to project the laser pulses into the eye tissue in a focused manner in order to break down eye tissue.

14. A device comprising:
a laser source configured to generate laser pulses;
a scanner system comprising at least one movable deflection mirror configured to dynamically deflect the laser pulses;
a projection optical unit for focused projection of the laser pulses in a projection direction;
a zoom system, which is arranged downstream of the scanner system and upstream of the projection optical unit, and configured to adjust the focused projection of the laser pulses in the projection direction in different zoom settings, wherein the zoom system has an optical axis and a virtual entry pupil which moves along the optical axis with the different zoom settings; and
a displacement device configured to displace the scanner system with respect to the virtual entry pupil of the zoom system with a translatory motion of the scanner system along the optical axis of the zoom system, depending on the zoom setting of the zoom system.

15. The device of claim 14, wherein the displacement device is configured to displace the scanner system in a synchronized manner with at least one of: the zoom setting of the zoom system, or an adjustment of the focused projection brought about by the zoom system.

16. The device of claim 14, wherein
the displacement device comprises a drive coupled to the scanner system and configured to displace the scanner system along the optical axis of the zoom system; and
the displacement device further comprises one or more circuits configured to generate positioning signals for controlling the drive depending on control signals for the zoom system or on feedback signals from the zoom system.

17. The device of claim 14, wherein the displacement device comprises:
a drive coupled to the scanner system and configured to displace the scanner system along the optical axis of the zoom system, and
one or more circuits configured to control the drive to displace the scanner system along the optical axis of the zoom system using a current zoom setting of the zoom system, to adapt a position of the scanner system, with respect to a current position of the virtual entry pupil of the zoom system, for continuously maintaining a value of distance of the scanner system from the virtual entry pupil of the zoom system.

18. The device of claim 14, wherein the displacement device comprises:
a drive coupled to the scanner system and configured to displace the scanner system along the optical axis of the zoom system; and
one or more circuits configured to control the drive to displace the scanner system along the optical axis to defined scanner positions with respective distances from the virtual entry pupil, the defined scanner positions including at least one of: a scanner position for performing cornea surgery and a scanner position for performing lens surgery.

19. The device of claim 14, further comprising a compensation system configured to optically compensate aberrations of the zoom system depending on a displacement of the scanner system and a deflection angle of the scanner system.

* * * * *